: US011717292B2

(12) United States Patent
Smith et al.

(10) Patent No.: US 11,717,292 B2
(45) Date of Patent: Aug. 8, 2023

(54) SYSTEMS, DEVICES, AND RELATED METHODS FOR FASTENING TISSUE

(71) Applicant: Boston Scientific Scimed, Inc., Maple Grove, MN (US)

(72) Inventors: Paul J. Smith, Smithfield, RI (US); Ramon Estevez, Lowell, MA (US); Allyn Narcisse Jensrud, Brookline, MA (US); Laura Christakis, Framingham, MA (US); Alec Orlofsky, New Rochelle, NY (US); Mingxiang Xu, Wayland, MA (US); Samuel Raybin, Marlborough, MA (US); Daniel Peter, West Newton, MA (US); John B. Golden, Norton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 530 days.

(21) Appl. No.: 16/804,887

(22) Filed: Feb. 28, 2020

(65) Prior Publication Data
US 2020/0275925 A1 Sep. 3, 2020

Related U.S. Application Data

(60) Provisional application No. 62/812,538, filed on Mar. 1, 2019.

(51) Int. Cl.
*A61B 17/072* (2006.01)
*A61B 17/29* (2006.01)
(Continued)

(52) U.S. Cl.
CPC ........ *A61B 17/07207* (2013.01); *A61B 1/018* (2013.01); *A61B 1/044* (2022.02);
(Continued)

(58) Field of Classification Search
CPC ...... A61B 2017/003; A61B 2017/2927; A61B 2017/2947
See application file for complete search history.

(56) References Cited

U.S. PATENT DOCUMENTS 3,490,675 A 1/1970 Green et al.
5,354,311 A * 10/1994 Kambin ................ A61B 17/29
606/205

(Continued)

FOREIGN PATENT DOCUMENTS

EP 1813211 A2 8/2007

*Primary Examiner* — Thanh K Truong
*Assistant Examiner* — Patrick B Fry
(74) *Attorney, Agent, or Firm* — Bookoff McAndrews, PLLC (57) ABSTRACT

According to one aspect, a tissue fastening device may include a handle assembly including at least two actuators. The tissue fastening device may also include a first body extending distally from the handle assembly and defining a longitudinal axis. The tissue fastening device may also include a fastening device coupled to a distal end of the first body. The fastening device may include a longitudinal body including a channel, a cartridge configured to include a plurality of fasteners, a longitudinal channel configured to receive a device for cutting tissue, an anvil rotatable relative to the cartridge, and a fastener actuator. The fastener actuator may be coupled to one actuator of the at least two actuators and configured to move proximally relative to the cartridge to deploy the plurality of fasteners from the cartridge.

20 Claims, 7 Drawing Sheets

(51) Int. Cl.
  *A61B 1/018*   (2006.01)
  *A61B 1/04*    (2006.01)
  *A61B 1/313*   (2006.01)
  *A61B 17/00*   (2006.01)

(52) U.S. Cl.
  CPC .......... *A61B 17/072* (2013.01); *A61B 1/3132* (2013.01); *A61B 2017/0034* (2013.01); *A61B 2017/07257* (2013.01); *A61B 2017/07271* (2013.01); *A61B 2017/07285* (2013.01)

(56) References Cited

U.S. PATENT DOCUMENTS

| | | | | |
|---|---|---|---|---|
| 7,506,791 | B2 * | 3/2009 | Omaits | A61B 17/072 227/181.1 |
| 7,725,214 | B2 * | 5/2010 | Diolaiti | A61B 5/0086 606/1 |
| 7,891,532 | B2 | 2/2011 | Mastri et al. | |
| 8,096,460 | B2 * | 1/2012 | Blier | A61B 17/07207 227/176.1 |
| 8,490,851 | B2 * | 7/2013 | Blier | A61B 17/068 227/176.1 |
| 8,562,592 | B2 * | 10/2013 | Conlon | A61B 17/3423 606/1 |
| 8,672,209 | B2 * | 3/2014 | Crainich | A61B 17/07207 227/19 |
| 11,160,552 | B2 * | 11/2021 | Kobayashi | A61B 17/07207 |
| 2010/0016659 | A1 | 1/2010 | Weitzner | |
| 2014/0076955 | A1 | 3/2014 | Lorenz | |
| 2015/0150620 | A1 * | 6/2015 | Miyamoto | A61B 18/1445 227/176.1 |
| 2019/0167267 | A1 * | 6/2019 | Kobayashi | A61B 17/115 |

\* cited by examiner

SYSTEMS, DEVICES, AND RELATED METHODS FOR FASTENING TISSUE

CROSS-REFERENCE TO RELATED APPLICATIONS

This application claims the benefit of priority from U.S. Provisional Application No. 62/812,538, filed Mar. 1, 2019, which is incorporated by reference herein in its entirety.

TECHNICAL FIELD

Various aspects of the present disclosure relate generally to tissue fastening, including visualizing, retracting, and coupling tissue. More specifically, at least certain embodiments of the present disclosure relate to systems, devices, and related methods for stapling tissue, among other aspects.

BACKGROUND

Technological developments have given users of medical systems, devices, and methods, the ability to conduct increasingly complex procedures on subjects. The coupling of tissue in, for example, a subject's gastrointestinal tract, is a type of procedure in which difficulties may arise. Surgical devices that grasp or clamp tissue between opposing jaw structures and then join the tissue by surgical fasteners are known. The fasteners include surgical staples. In some procedures, a cutting instrument is provided to cut the tissue which has been joined by the fasteners. However, problems arise when stapling and cutting tissue in order to remove tumorous tissue from a patient's body.

One such difficulty involves removing a lesion from tissue. In order to remove a lesion, the user may staple tissue around the outer edge of the lesion. When a lesion is highly contagious, it is important to cut the tissue at a region that does not include the lesion to avoid spreading the contagious tissue. There is a need for stapler instruments that include both stapling and cutting features that address this difficulty.

Often surgical staplers include a staple cartridge to house a plurality of staples. An anvil defines a surface for forming the staple legs as the staples are driven from the staple cartridge. The stapling operation may be effected by an actuator acting upon a staple, which often involves pushing the actuator in a distal direction to drive the staples from the cartridge. With such a configuration, problems arise when pushing the actuator due to curves in portions of the stapler connecting its proximal and distal ends, and a user may find it difficult to actuate the stapler when the stapler is rotated or angled from a longitudinally straight position.

Another difficulty involves removing a lesion from tissue by stapling its outer perimeter and cutting the lesion from the tissue. In order to remove the lesion, the user may first staple tissue around the lesion. When stapling, the user may need to clearly observe the outer edge of the lesion, however the user's field of view may be obstructed by the stapler if the distal end of the stapler is longitudinal rigid or fixed, preventing the instrument from bending and moving out of the field of view of the user. For example, during an endoscopic procedure, the optics of the endoscope often are positioned immediately adjacent the tissue, resulting in poor recognition of the endoscope location relative to the rest of the body lumen or larger tumors.

SUMMARY

Aspects of the disclosure relate to, among other things, systems, devices, and methods for fastening tissue. Each of the aspects disclosed herein may include one or more of the features described in connection with any of the other disclosed aspects.

According to one aspect, a tissue fastening device may include a handle assembly including at least two actuators. The tissue fastening device may also include a first body extending distally from the handle assembly and defining a longitudinal axis. The tissue fastening device may also include a fastening device coupled to a distal end of the first body. The fastening device may include a longitudinal body including a channel, a cartridge configured to include a plurality of fasteners, a longitudinal channel configured to receive a device for cutting tissue, an anvil rotatable relative to the cartridge, and a fastener actuator. The fastener actuator may be coupled to one actuator of the at least two actuators and configured to move proximally relative to the cartridge to deploy the plurality of fasteners from the cartridge.

In other aspects of the disclosure, the tissue fastening device may include one or more of the features below. The tissue fastening device may include a protrusion extending from a side surface of the fastening device and defining a lumen configured to receive a tissue acquisition tool. The fastening device may include a device for cutting tissue. The fastener actuator may be coupled to an actuation wire that extends from the fastener actuator through the elongated body to the handle assembly, and the actuation wire may be coupled to a first actuator of the at least two actuators. The fastener actuator may be configured to move proximally relative to the cartridge and the anvil when the first actuator is actuated. A distal portion of the first body may include a rigid curved portion such that a longitudinal axis of the fastening device is transverse to a longitudinal axis of a proximal portion of the first body. The anvil may include a first recess, the longitudinal body may include a second recess opposing the first recess, and the first and second recesses may be configured to receive a tissue acquisition tool. The fastener actuator and the device for cutting tissue may be coupled to an actuation wire that extends from the fastening device through the first body to a first actuator of the handle assembly, and the first actuator may be configured to move both the fastener actuator and the device for cutting tissue proximally. The fastening device may be rotatably coupled to the first body. The fastener actuator may include a ramp, and a surface of the ramp that contacts the plurality of fasteners may have an angle of 30 degrees or less relative to a longitudinal axis of the longitudinal body. The fastening device may be fixedly coupled to the first body, and a longitudinal axis of the fastening device may be transverse to a longitudinal axis of the first body.

In other aspects, a tissue fastening device may include a handle assembly including at least two actuators. The tissue fastening device may also include a first body extending distally from the handle assembly and defining a longitudinal axis. The tissue fastening device may further include a fastening device coupled to a distal end of the first body. The fastening device may include a longitudinal body including a channel. The fastening device may also include a cartridge that includes a plurality of fasteners. The fastening device may further include an anvil mounted adjacent the cartridge. The tissue fastening device may also include a second body including a lumen. The first body may be positioned in, movable within, and extends from the lumen. The tissue fastening device may also include a coupler coupling a distal end of the second body to the fastening device. The fastening device may be pivotable about the coupler when the first body is moved proximally and/or distally.

In other aspects of this disclosure, the tissue fastening device may further include one or more of the features below. The second body may define an opening in a side wall of the second body and through which the first body extends. The second body may include a recess configured to receive a portion of the first body when the longitudinal axis of the fastening device is parallel to the longitudinal axis of the second body. The handle assembly may include a first actuator configured to move longitudinally in proximal and distal directions and a second actuator configured to pivot relative to a body of the handle assembly.

In other aspects of this disclosure, a system may include a tissue fastening device and a tissue acquisition tool moveably coupled to the tissue fastening device. The system may also include an overset including a distal end opening and at least two distal end portions. The overset may be positioned around the tissue fastening device and the tissue acquisition tool. The overset may be configured to move proximally and the at least two distal end portions may be configured to move radially outward, to expose the tissue fastening device and tissue acquisition tool.

In other aspects, the system may further include one or more of the features below. A longitudinal body including a channel and a guide protrusion. The guide protrusion may include a lumen configured to receive the tissue acquisition tool. The tissue fastening device may further include a cartridge including a plurality of fasteners; and an anvil mounted adjacent the cartridge. The tissue acquisition tool may be positioned within the lumen of the guide protrusion. A proximal portion of the overset may be positioned around an endoscope, and the endoscope may include an image sensor and at least two working channels. The at least two distal end portions may be biased radially inward and configured to partially enclose fastening device and tissue acquisition tool.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects of the present disclosure and together with the description, serve to explain the principles of the disclosure.

DETAILED DESCRIPTION

The present disclosure is drawn to systems, devices, and methods for coupling, cutting, and resecting tissue, among other aspects. Reference will now be made in detail to aspects of the present disclosure, examples of which are illustrated in the accompanying drawings. Wherever possible, the same or similar reference numbers will be used through the drawings to refer to the same or like parts. The term "distal" refers to a portion farthest away from a user when introducing a device into a patient. By contrast, the term "proximal" refers to a portion closest to the user when placing the device into the patient. The term "coupling tissue together" may refer, for example, to stapling, fixing, attaching, fastening, or otherwise joining two portions of tissue together. The term "fastener" may include staples, clips, elastic bands, suture, or any other fastener known in the art. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal."

Embodiments of the present disclosure may be used to visualize, cut, resect, and/or couple together target tissue in an endo-luminal space, or facilitate the process thereof. In particular, some embodiments combine a tissue resecting device with a tissue stapling device. The tissue stapling apparatus may include a resection or cutting mechanism (e.g., an integrated knife) and a stapling mechanism (stapler). The stapling apparatus may be delivered to target tissue through an endoscope working channel to the target tissue site. The overall system may include a retraction mechanism, such as a tissue clip, to pull tissue towards the tissue stapling device. All or parts of the tissue stapling device and the retraction mechanism could be metallic, plastic, or include a shape memory metal (such as nitinol), a shape memory polymer, a polymer, or any combination of materials.

Figure 1:
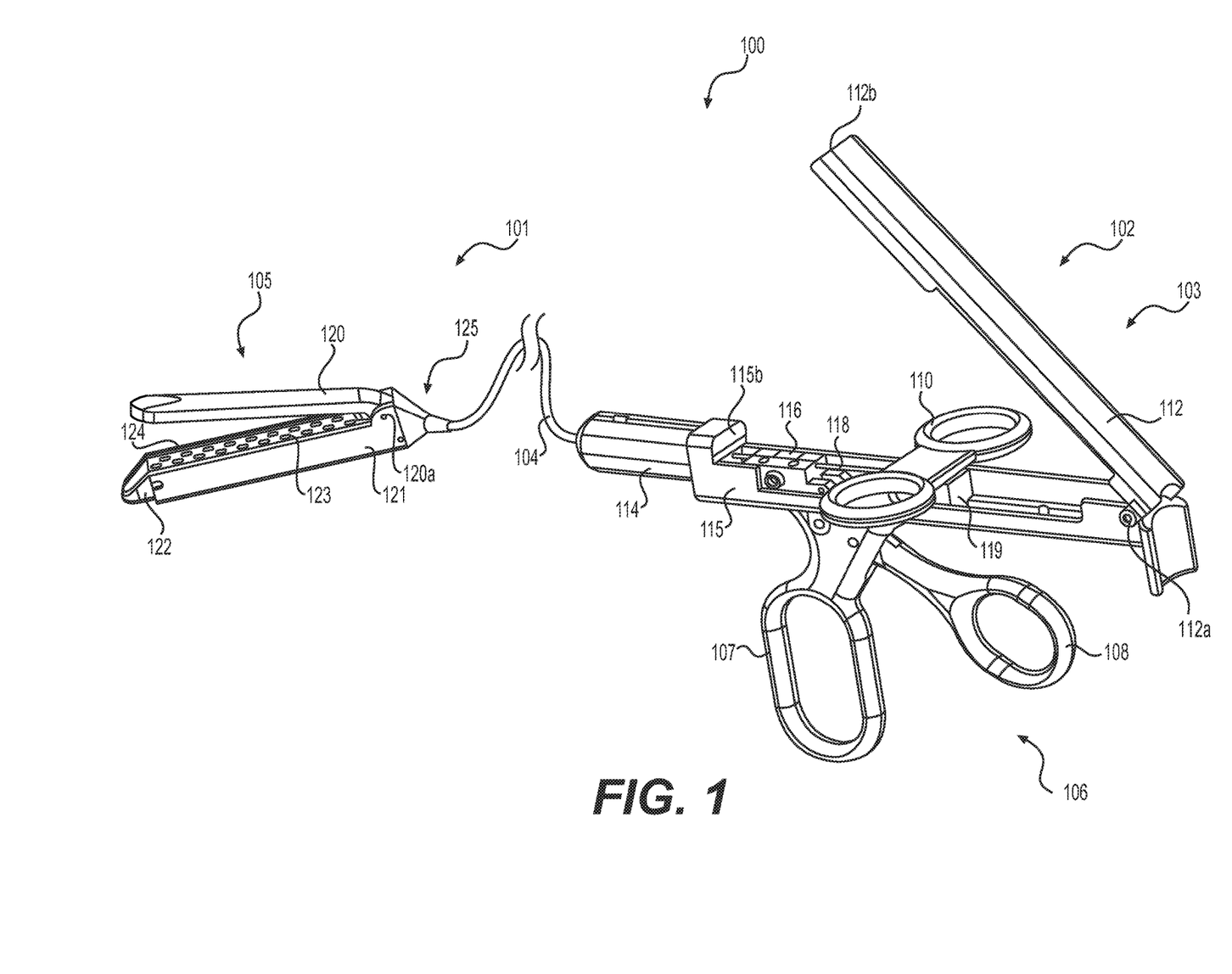
FIG. 1 is a perspective view of an exemplary medical device, according to aspects of this disclosure.

FIG. 1 shows a surgical apparatus 100 in accordance with an embodiment of this disclosure. Apparatus 100 is a surgical stapling apparatus configured to engage body tissue, apply a plurality of surgical fasteners thereto, and form an incision in the fastened body tissue during minimally invasive surgical procedures, such as laparoscopic or endoscopic procedures. Apparatus 100 may be used to apply surgical clips or other fasteners, but will be primarily discussed in the context of applying staples from a staple cartridge positioned in a portion of the device's body, such as a loading unit.

As illustrated in FIG. 1, apparatus 100 includes a distal section 101 and a proximal section 102. Surgical apparatus 100 also includes a handle assembly 103, an elongate body 104, and a stapler device 105. The elongate body 104 may extend any length suitable for endoscopic or laparoscopic procedures, and may be configured to be positioned within a working channel of an endoscope. The elongate body 104 may be detachable from the handle assembly 103 to facilitate insertion of the elongate body 104 into a working channel of an endoscope or a channel of another device, for example by backloading body 104 into the working channel. In some examples, the elongate body may be flexible and/or may be rotatable about its axis. The elongate body 104 may include a lumen for positioning actuation wires within for actuating the stapler device 105 via the handle assembly 103 or actuating any other portion of the apparatus 100. The elongate body 104 may be configured to receive a plurality of actuation wires or a single actuation wire (for example, actuation wire 118). In some examples, the elongate body 104 may be fixedly coupled to the stapler device 105, and in other examples the elongate body 104 may be removably or releasably coupled to the stapler device 105.

The handle assembly 103 may include a handle 106 and a body 115. The handle 106 may include a fixed portion 107 and an actuator portion 108. Fixed portion 107 of handle 106 may be fixedly coupled to body 115, and fixed portion 107 may include a circular or oval portion or ring for positioning a user's fingers within, which may assist a user in holding the handle assembly 103. In some examples, moveable portion 108 of handle 106 may be an actuator which may be pivotally coupled to body 115 and movable relative to the fixed portion 107 of handle 106. Movable portion 108 may include a circular or oval portion for positioning a user's fingers within, which may assist in actuating surgical apparatus 100. In some examples, movable portion 108 of handle 106 may be coupled to a proximal portion of an actuation wire, such as actuation wire 118, via an adjustable coupler 116 and may be configured to actuate an anvil of stapler device 105 via actuation wire 118 extending between stapler device 105 and handle assembly 103. In other examples, movable portion 108 of handle 106 may be configured to control any other mechanism of apparatus 100, such as actuation of deploying staples from stapler device 105.

In some examples, handle assembly 103 may include a moveable cover 112 pivotably coupled to housing 115 at pivot point 112a. In FIG. 1, cover 112 is shown in an open position, exposing the internal portions of housing 115. Cover 112 may be coupled to a proximal portion of housing 115 and may cover the internal components of handle assembly 103 when positioned longitudinally parallel to housing 115, such that distalmost end 112b of cover 112 faces surface 115b of housing 115. Cover 112 may be temporarily fixedly coupled to a position covering the internal components of housing 115 via a coupling mechanism at a distal portion of cover 112 and a distal portion of handle assembly 103, such as a snap locking mechanism, in order to hold cover 112 in place and prevent movement of cover 112 relative to housing 115. When held in place, cover 112 may form a pair of slots in housing 115 (not shown). When the distal portion of cover 112 is uncoupled from the distal portion of housing, a user may rotate (or pivot) cover 112 at pivot point 112a in order to have access to the internal components of handle assembly 103.

Handle assembly 103 may further include a rotatable elongate connector 114 which may connect the elongate body 104 to handle assembly 103. In some examples, rotatable elongate connector 114 may rotate relative to housing 115 to either tighten onto elongate body 104 in order to fixedly couple elongate body 104 to handle assembly 103, or rotated to release elongate body 104 from handle assembly 103. Within body 115, one or more adjustable couplers 116, 119 may be positioned in longitudinal alignment with, or longitudinally parallel with, rotatable elongate connector 114 and may be configured to receive a portion of an actuation wire, such as actuation wire 118. Any of adjustable couplers 116, 119 may be a vice which is moveable in order to clamp down onto an actuation wire and fixedly couple actuation wire to the adjustable coupler 116, 118. In some examples, adjustable coupler 116, 119 may be moveable via a screw to adjust the coupler 116, 119 and couple or uncouple an actuation wire from coupler 116, 119.

Adjustable coupler 119 may be coupled to longitudinal actuator 110 and moveable longitudinally via translating longitudinal actuator 110 within housing 115. Longitudinal actuator 110 may be partially positioned within housing 115 and may be slidable longitudinally within two slots formed when cover 112 is positioned over the internal components of handle assembly 103. Longitudinal actuator 110 may include a pair of opposing circular or oval portions or rings, with each circular portion defining an aperture for a user to position their fingers within. In some examples, longitudinal actuator 110 may be coupled to an actuation wire (not shown), such as via adjustable coupler 119 or via a different coupler within housing 115, and may be configured to control staple deployment from stapler device 105. In other examples, longitudinal actuator 110 may be configured to control any other mechanism of apparatus 100, such as actuation of an anvil of stapler device 105.

Distal section 101 of apparatus 100 includes a stapler device 105 coupled to a distal portion of elongate body 104. A connector 125 of stapler device 105 may couple elongated body 104 to stapler device 105. In some examples, connector 125 may be offset from a longitudinal axis of the body 121 of stapler device 105. Body 121 of stapler device 105 may include a cartridge 122 positioned within a channel of body 121. Cartridge 122 may be fixedly coupled to body 121 or may be removable from body 121. In some examples, cartridge 122 may be integrally formed in body 121. At a proximal portion of body 121, an anvil 120 may be rotatably or pivotably coupled to body 121 at pivot axis 120a, and may extend distally towards a distal end of stapler device 105. In some examples, anvil 120 may be rotatably biased and may be biased to an open configuration, i.e. biased away from body 121 and cartridge 122 creating a space between the distal portion of anvil 120 and the distal portion of body 121 and cartridge 122. Anvil 120 may be rotatable about axis 120a to contact body 121, or pinch tissue between anvil 120 and body 121, and provide a surface for which staples may be driven when ejected from cartridge 122.

In some examples, body 121 may include a channel that supports cartridge 122. Cartridge 122 may contain a plurality of surgical fasteners, such as staples, and the fasteners may be deployed from cartridge 122 when under the influence of a driving force exerted by an actuation sled, such as actuation sled 341 shown in FIG. 3A. A plurality of spaced apart longitudinal slots 123 in cartridge 122 allow staples to pass through cartridge 122 and pierce tissue. In some examples, an actuation sled moves proximally in the longitudinal direction from a distal end of cartridge 122 and/or body 121 when actuated, contacting fasteners within cartridge 122 and pushing fasteners through longitudinal slots 123 in order to couple fasteners to tissue. In some examples, a single fastener may extend through each slot 123. Each fastener may be partially within a slot 123 prior to deployment to assist with alignment of the fastener with the slot 123. In some examples, two actuation sleds 341, 380 may be required to actuate two different longitudinal rows of fasteners in cartridge 122 (shown in FIG. 3A).

Cartridge 122 may also include an elongate longitudinal slot 124. The elongate longitudinal slot 124 may be configured to receive and/or support a resecting tool, such as a knife blade (not shown). The elongate longitudinal slot 124 may be positioned on a side of cartridge 122 and may run longitudinally from the proximal end to the distal end of cartridge 122. In some examples, each of the spaced apart longitudinal slots 123 may be positioned on one side of the elongate longitudinal slot 124. Anvil 120 may include a groove (not shown) positioned longitudinally that may align with elongated longitudinal slot 124 when anvil 120 is in the closed position (i.e. anvil 120 is rotated such that a distal portion of anvil 120 comes into contact with body 121 and/or cartridge 122, or pinches tissue between anvil 120 and body 121) and such groove may be configured to receive a resecting tool such as a knife or other sharp cutting tool within the elongate longitudinal slot 124. The cutting tool may be actuated via an additional, separate actuation wire from the actuation wire that translated the actuation sled, or may be actuated via the same actuation wire as the actuation sled to translate both the actuation sled and the cutting tool at the same time.

A user may use apparatus 100 to couple one or more fasteners to tissue by first positioning tissue within the active region of stapler device 105, or between body 121 and anvil 120. Once tissue is positioned in the active region of stapler device 105, a user may actuate the actuator portion 108 of handle 106, which may then translate an actuation wire proximally and cause anvil 120 to close onto the tissue positioned within the stapler device's active region. While the user holds actuation portion 108 in an engaged position, thus maintaining the stapler device's clasp on the tissue, the user may pull proximally (or actuate) longitudinal actuator 110 to translate an actuation wire coupled to an actuation sled in the stapler device. When the actuation sled is translated proximally via the actuation wire coupled to the longitudinal actuator 110, a ramp of the actuation sled may engage a fastener in cartridge 122 and push the fastener through a longitudinal slot 123 to pierce the tissue. When the fastener is deployed by the actuation sled, the fastener may subsequently engage anvil 120 and couple layers of tissue together. In some examples, the longitudinal actuator 110 may actuate an actuation wire coupled to both an actuation sled and a cutting tool, and may translate both the actuation sled and the cutting tool simultaneously to both pierce and fasten tissue with one or more fasteners and cut tissue.

In some examples, a user may backload elongate body 104 through the distal end of a working channel of an endoscope, through the body of the endoscope, and out of a proximal end of the endoscope prior to coupling the elongate body 104 to the handle assembly 103. Once elongate body 104 is positioned within a working channel of an endoscope with stapler device 105 at the endoscope's distal end, a user may couple handle assembly 103 to elongate body 104 by inserting the proximal end of elongate body 104 into rotatable elongate connector 114, and then rotating rotatable elongate connector 114 to fix elongate body 104 to handle assembly 103. A user may then couple the proximal ends of actuation wires (such as actuation wire 118) positioned within elongate body to adjustable couplers 116, 119. Once elongate body 104 is coupled to handle assembly 103 and actuation wires (such as actuation wire 118) are coupled to adjustable couplers 116, 119, the user may close moveable cover 112 such that distalmost end 112b of cover 112 faces surface 115b of housing 115. Cover 112 may be temporarily fixedly coupled to a position covering the internal components of housing 115 via a coupling mechanism at a distal portion of cover 112, and a distal portion of handle assembly 103, such as a snap locking mechanism, in order to hold cover 112 in place during use of apparatus 100.

Figure 2:
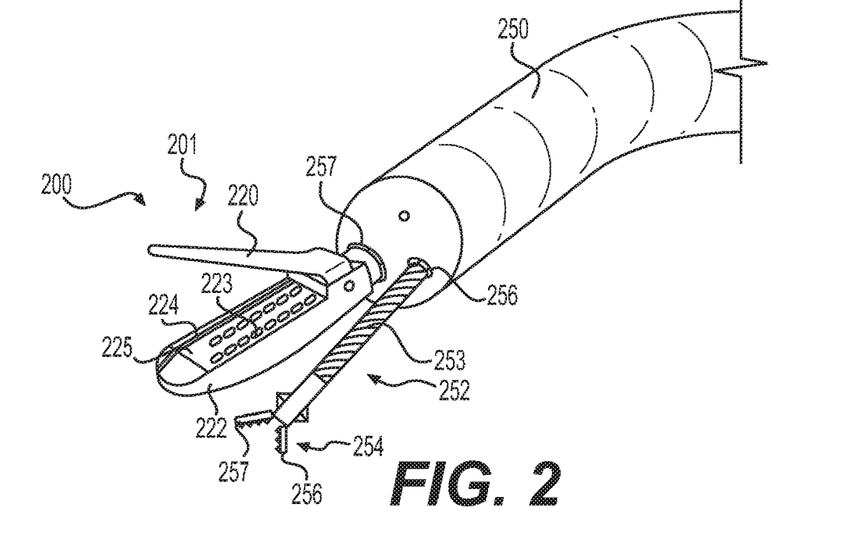
FIG. 2 is a perspective view of an exemplary surgical system, according to aspects of this disclosure.

FIG. 2 shows a distal section of an endoscope 250, a tissue acquisition tool 252 positioned within a working channel 256 of the endoscope 250, and a surgical apparatus 200 positioned within another working channel 257 of the endoscope 250, in accordance with an embodiment of this disclosure. Surgical apparatus 200 is substantially similar to surgical apparatus 100 and includes a stapler device 201 with longitudinal slots 223 for fastener deployment, an elongated longitudinal slot 224 for receiving a knife, and anvil 220. Cartridge 225 is integrally formed in body 222 of stapler device 201. A user may use a tissue acquisition tool 252 in combination with a stapler device, such as stapler device 201, to facilitate grabbing tissue and positioning tissue in the active portion of stapler device 201, i.e. between body 222 and anvil 220 for stapling. Tissue acquisition tool 252 may include an elongate body 253 extending longitudinally to a distal end portion 254. In some examples, distal end portion 254 of tissue acquisition tool 252 may include a pair of rotatable jaws 256, 257 that are moveable between a closed configuration and an open configuration. A user may actuate jaws 256, 257 using an actuator present at the proximal portion of tissue acquisition tool 252 (not shown) to open and close jaws 256, 257 to facilitate grabbing and releasing tissue. A user may position tissue acquisition tool 252 within a working channel 256, as shown in FIG. 2, separate from the working channel 257 in which the surgical apparatus 200 is positioned. In other examples, a user may position tissue acquisition tool 252 in the same working channel as surgical apparatus 200 (not shown) to facilitate positioning tissue between anvil 220 and body 222.

Figures 3A, 3B:
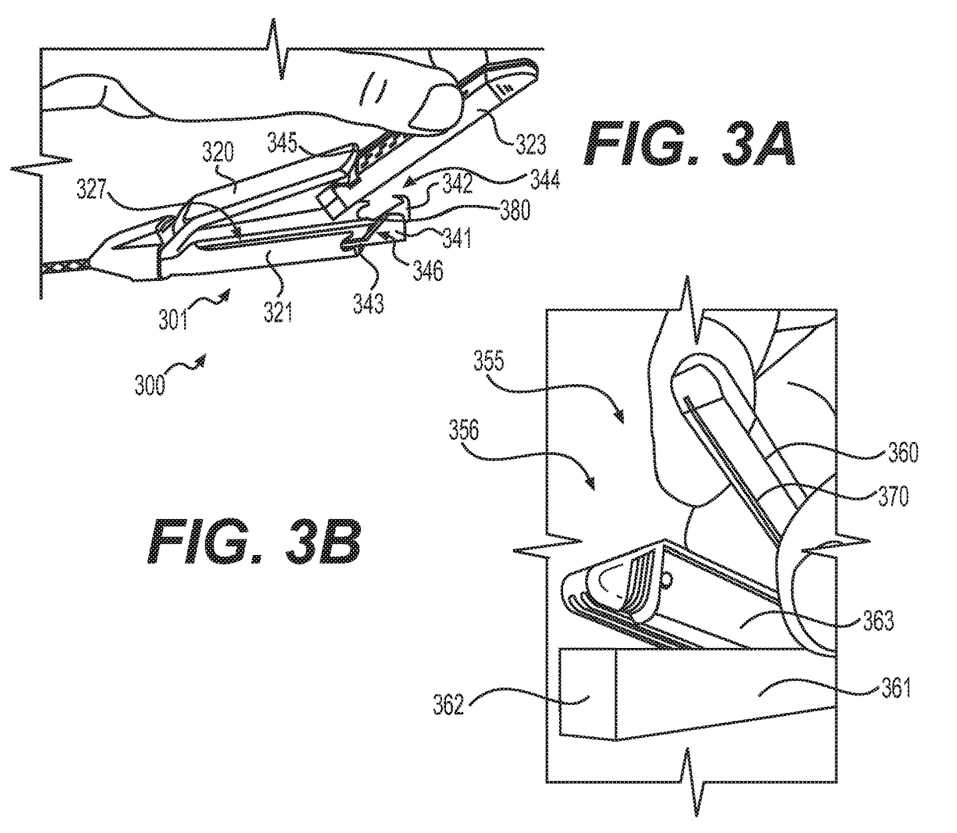
FIG. 3A is a perspective view of an exemplary medical device, according to aspects of this disclosure, including a component being inserted into the device by a user.
FIG. 3B is a perspective view of a portion of an exemplary medical device, according to aspects of this disclosure, with a component being inserted into the device by a user.

FIG. 3A shows a distal portion of an embodiment of surgical apparatus 300 including stapler device 301 that is configured to receive a removable cartridge 323. When removable cartridge 323 is removed from body 321, actuation sled 341 and knife 342 may be visible (shown in FIG. 3A). In some examples, when cartridge 323 is positioned within a channel 327 of body 321, actuation sled 341 and knife 342 may be received within cartridge 323 and may not be visible. In other examples, actuation sled 341 and knife 342 may be received within cartridge 323 and may be visible when cartridge 323 is positioned within body 321, such as by extending out of a channel in cartridge 323. Actuation sled 341 and knife 342 may be coupled to a single actuation wire extending to a proximal portion of surgical apparatus 300 such that, when actuated, the actuation sled 341 and knife 342 move proximally in unison. In other examples, actuation sled 341 and knife 342 may be coupled to separate actuation wires extending from a proximal portion of either actuation sled 341 or knife 342 to a proximal portion of surgical apparatus 300, such as to handle assembly 103 such that either the actuation sled 341 or the knife 342 may be actuated independently. Actuation sled 341 may be configured to be translated proximally to push fasteners, such as staples within cartridge 323, out of slots 345 in cartridge to fasten tissue together. Actuation sled 341 and knife 342 may be pressed by the user into a distal pocket of cartridge 323 when cartridge 323 is first positioned within body 321.

Actuation sled 341 may include a ramp 346 that is configured to engage, directly or indirectly, staples, or other fasteners from within cartridge 323 through slots 345, to deploy fasteners to couple tissue. In some examples, ramp 346 may be angled at 45 degrees, 40 degrees, 35 degrees, 30 degrees, 25 degrees, or any other angle relative to a longitudinal axis of body 321. Ramp 341 may be a shallow angle to require the actuation sled 341 to translate proximally for a longer distance in order to deploy fasteners in cartridge 323. By providing actuation sled 341 with a shallow angle, long ramp 341, a user may engage multiple fasteners at the same time when pulling actuation sled 341 proximally, and thus allowing, in some examples, multiple staples to deploy and pierce tissue at the same time. Furthermore, a shallow angle ramp 346, e.g. an angle approximately 30 degrees or less, may prevent intermittent forces being applied to the actuator in the handle assembly due to the actuation sled 341 releasing from a fastener before engaging the next fastener, by continuously engaging fasteners in cartridge 323, and thus may prevent errors during a procedure by providing a more continuous force applied to the actuator. In some examples, the ramp 346 of actuation sled 341 may engage two, three, four, or more fasteners in cartridge 323 at the same time. Since actuation sled 341 is pulled proximally to deploy fasteners, a user may generate higher loads when pulling a flexible wire, such as an actuation wire 118 shown in FIG. 1, compared to a pushing mechanism to deploy fasteners. An actuation body 343 may extend proximally from a proximal portion of ramp 346, and actuation sled 341 may be pulled from the actuation body 343 to deploy fasteners. For example, actuation body 343 may be coupled to an actuation wire that extends to a proximal portion of the surgical apparatus 300. In some examples, apparatus 300 may include two actuation sleds 341 and two actuation bodies 343 coupled to the same actuation wire to engage and deploy two separate rows of fasteners in cartridge 323.

Knife 342 may have a similar structure to actuation sled 341 and may include a hooked distal portion 344 that includes sharp edges for cutting tissue. Knife 342 may be configured to travel longitudinally within an elongated longitudinal slot of cartridge 323. In some examples, a portion of knife 342 extends into a groove of anvil 320, such as groove 370 shown in FIG. 3B, and travels within the groove longitudinally from the distal end of anvil 320 to the proximal end when a user actuates knife 342, thus translating knife 342 longitudinally across cartridge 323 to cut tissue.

FIG. 3B shows a distal portion of an alternative embodiment of surgical apparatus 355 including stapler device 356 that is configured to receive a removable cartridge 363. In stapler device 356, body 361 includes a distal end with a distal front face 362 that encloses cartridge 363 within body 361 with only the top portion of cartridge 363, or the portion of cartridge 363 opposing a bottom surface of anvil 360, exposed. Distal front face 362 prevents the distal end of cartridge 363, or in some examples an actuation sled and/or a knife, from contacting tissue when moving stapler device 356. Anvil 360 includes a groove 370 within a surface opposing cartridge 363, configured to receive a knife when anvil 360 is in a closed position.

Figure 4A:
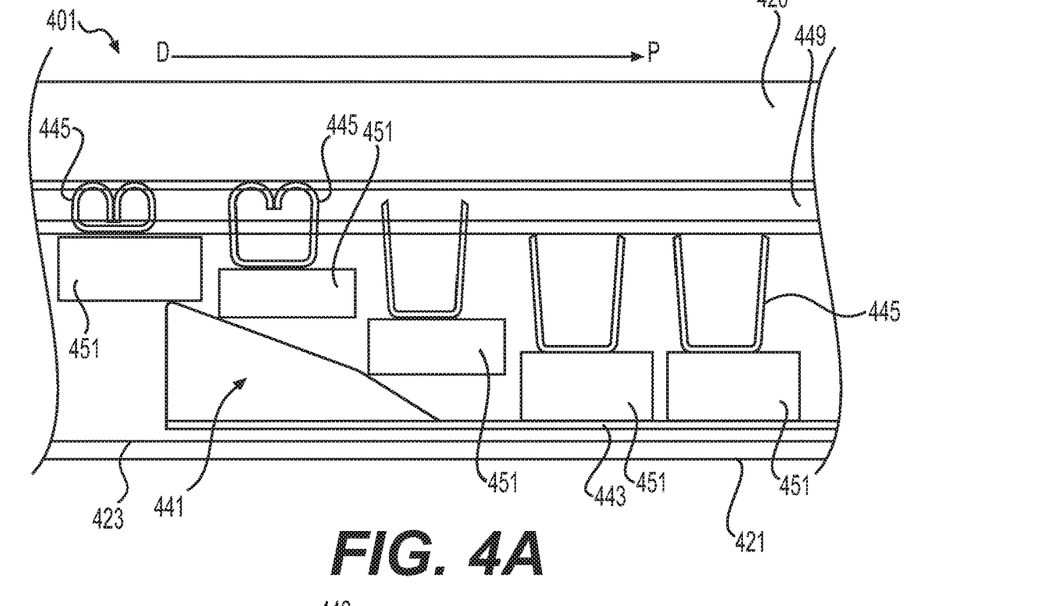
FIG. 4A is a cross-sectional view of a portion of an exemplary medical device, according to aspects of the present disclosure.

FIG. 4A shows an enlarged, cross-sectional view of an exemplary stapler device 401 including body 421, anvil 420, cartridge 423 with fasteners 445, and actuation sled 441 with actuation body 443. The stapler device 401 in FIG. 4A is shown deploying fasteners 445 onto tissue 449. Actuation sled 441 engages pistons or spacers 451, and the pistons or spacers 451 then engage the fasteners 445 to deploy the fasteners 445. As shown in FIG. 4A, actuation sled 441 engages the pistons or spacers 451 as actuation sled 441 moves in the proximal direction P. Each piston or spacer 451 may be configured to translate within cartridge 423 and may be sized to engage only one fastener. In other examples, each piston or spacer 451 may be sized to engage multiple fasteners, or one or more pistons or spacers 451 may be sized to engage multiple fasteners while one or more other pistons or spacers 451 may be sized to engage only one fastener. Actuation sled 441 may be configured to move each piston or spacer 451 in a direction transverse to the longitudinal axis of body 421. For example, actuation sled 441 and actuation body 443 may be pulled proximally via an actuation wire, which may move ramp 442 (shown in FIG. 4B) into contact with one or more pistons or spacers 451 and push one or more pistons or spacers 451 to deploy one or more fasteners 445 from cartridge 423. Each of the pistons or spacers 451 may have an upper surface that aligns and/or is flush with a portion of each respective fastener 445. For example, each fastener 445 may be a staple and may include three substantially flat sections with the middle substantially flat section aligning with the top surface of each spacer 451. Each piston or spacer 451 may be sufficiently rigid to move uniformly upward when the ramp 442 of actuation sled engages a corner of the piston or spacer 451. In some examples, each piston or spacer 451 may be coupled to cartridge 423 such that movement along the longitudinal axis of cartridge 423, or in the proximal P or distal D directions shown in FIG. 4A, is prevented while allowing movement in a direction perpendicular to the longitudinal axis of cartridge 423. The pistons or spacers 451 in cartridge 423 may prevent fasteners 445, such as staples, from partially deploying and may avoid improper stapling caused by a distal portion of a staple moving upward when a proximal portion of the staple does not move. By providing spacers 451 with flat top surfaces that align with fasteners 445, the ramp 442 of actuation sled 441 can move proximally and push each fastener 445 uniformly upward by engaging each spacer.

Figure 4B:
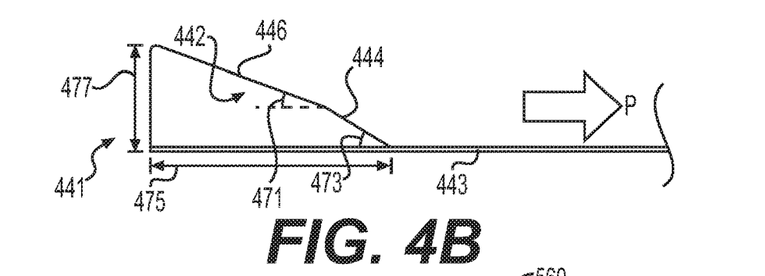
FIG. 4B is a side view of an exemplary actuation sled, according to aspects of the present disclosure.

FIG. 4B shows an exemplary actuation sled 441 including a ramp 442, a width 475, a height 477, and an actuation body 443. Ramp 442 may include a first proximal section 444 and a second distal section 446. In some examples, the first proximal section 444 may have a different incline angle 473 than the incline angle 471 of the second distal section 446. For example, the first proximal section 446 may have an incline angle of 30 degrees and the second distal section may have an incline angle of 20 degrees. By varying the slope of ramp 442, actuation sled 441 may push spacers 451 with varying levels of pressure as it moves proximally. In other examples, the first proximal section 446 and the second distal section 446 may have the same incline angles 471, 473 or they may have any other angle between 0 and 90 degrees. In some examples, actuation sled 441 may have a length 475 of 0.50 inches and a height of 0.215 inches. Actuation body 443 may extend from the bottom of ramp 442 and, in some examples, may also extend the length 475 of the actuation sled 441. In some examples, actuation body may be 0.008 inch diameter stainless steel wire.

FIG. 4B shows a partial cross-sectional view of an exemplary actuation sled 441, a portion of an anvil 420 including a recess 450 in the anvil's surface that faces cartridge 423, a portion of a cartridge 423, a fastener 445, and tissue 449 positioned between cartridge 423 and anvil 420. When actuation sled 441 is actuated, for example pulled from its proximal end 443 proximally via an actuation mechanism such as an actuator in handle assembly 103, ramp 442 will engage fastener 445 and translate fastener towards tissue 449 to pierce tissue 449 as the actuation sled 441 moves in the proximal direction. In other examples, a pin may be positioned between fastener 445 and actuation sled 441, and ramp 442 may engage the pin instead of fastener 445, the pin forcing the fastener 445 towards tissue 449. When fastener 445 is translated through tissue 449 via engagement with actuation sled 441, portions of fastener 445 may be pushed towards each other via engagement with recess 450 and may cause fastener to clasp onto tissue 449.

Figure 5A:
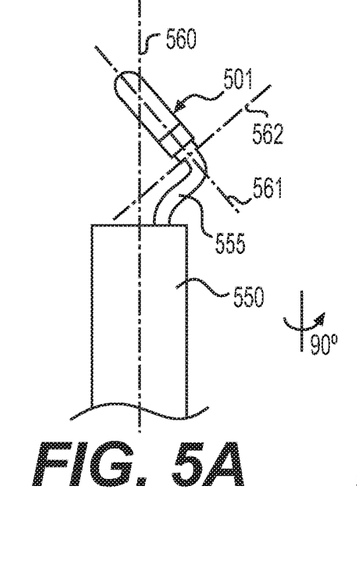
FIGS. 5A and 5B are perspective views of exemplary medical devices, according to aspects of this disclosure.
Figure 5B:
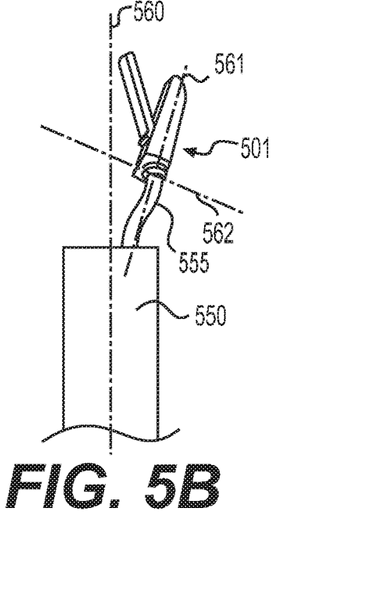

FIG. 5A shows an exemplary stapler device 501 that is angled relative to the longitudinal axis 560 of endoscope 550 and radially displaced from the endoscope's longitudinal axis 560. Elongate body 555 may include a distal end exposed from the endoscope, the distal end may be biased into a curved orientation (shown in FIG. 5A) such that the longitudinal axis 561 of the stapler device 501 intersects the longitudinal axis 560 of the endoscope 550 in which a portion of elongate body 555 is positioned within. In some examples, the angle formed between the longitudinal axis 561 of stapler device 501 and the longitudinal axis 560 of the endoscope 550 may be fifteen degrees, thirty degrees, forty-five degrees, sixty degrees, or any other angle. Alternatively, the distal end of body 555 may include links or other structure that causes the distal end to be in a rigid or substantially rigid configuration shown in FIG. 5A. FIG. 5B shows an alternative view of stapler device 501 in which elongate body 555 has been rotated ninety degrees to position stapler device 501 such that the longitudinal axis 561 of stapler device 501 is angled away from the longitudinal axis 560 of endoscope 550. Axis 562 shows an axis perpendicular to longitudinal axis 560. By having an elongate body 555 that is rigidly curved or otherwise biased curved to angle the longitudinal axis 561 of stapler device 501 relative to the longitudinal axis 560 of endoscope 550, the user's working space may be modified to allow for greater visualization, for example visualization through a camera positioned at the distal end of endoscope 550. Other benefits of angling stapler device 501 relative to the longitudinal axis of endoscope 550 may include facilitating alignment with a tissue acquisition tool and aiding in positioning tissue between the anvil and the body of stapler device 501. In some examples, elongated body 555 may be articulable to angle and radially offset stapler device 501. Body may be articulated via articulation links activated at a proximal end of endoscope 550.

Figure 6A:
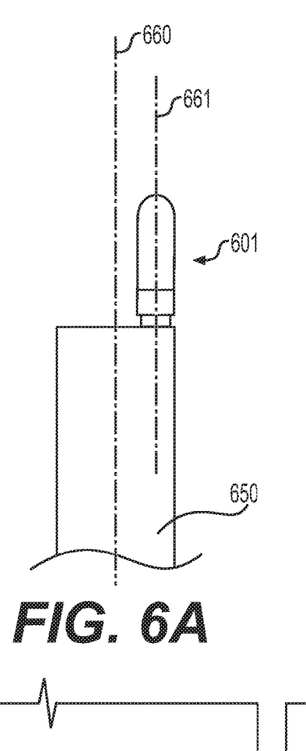
FIGS. 6A and 6B are perspective views of exemplary medical devices, according to aspects of this disclosure.
Figure 6B:
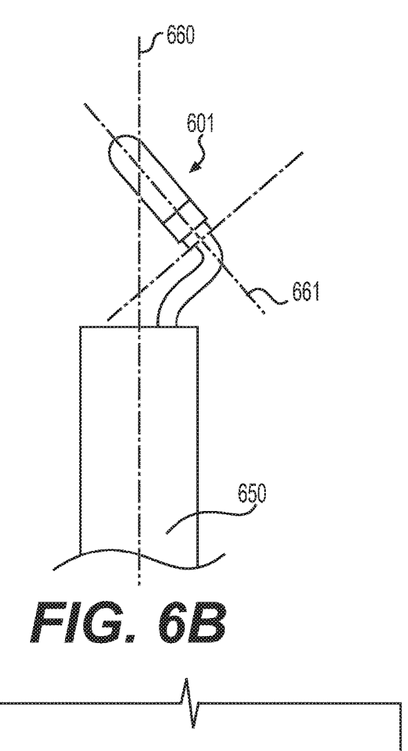

FIGS. 6A and 6B show an example of a center line 660 of a field of view of a camera at the distal end of endoscope 650. In FIG. 6A, the longitudinal axis 661 of stapler device 601 is parallel to the center line 660, and thus stapler device 601 is positioned on a side of the field of view. FIG. 6B shows stapler device 601 angled relative to the center line 660 of a field of view of a camera. In FIG. 6B, by pushing stapler device 601 distally and articulating the elongate body attached to it, the longitudinal axis 661 intersects with the center line 660 and positions the distal end portion of stapler device 601 directly within the center of the field of view of the camera of endoscope 650.

Figure 7A:
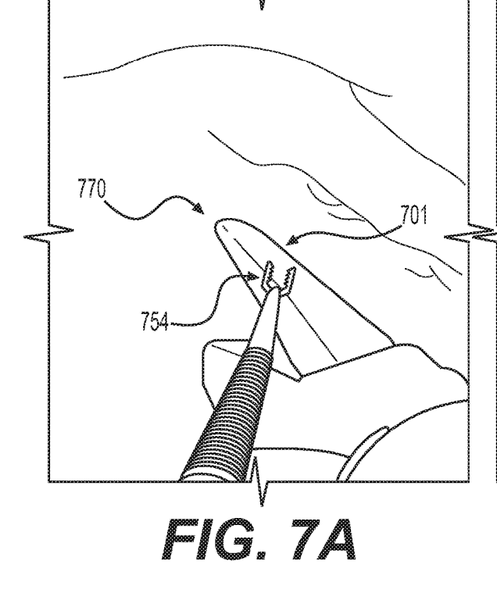
FIGS. 7A and 7B are perspective views of exemplary fields of view of an exemplary endoscopic system, according to aspects of this disclosure.
Figure 7B:
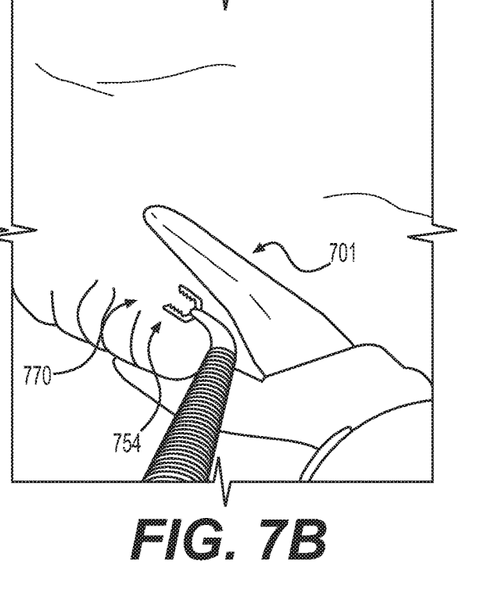

FIGS. 7A and 7B show a field of view of a camera at a distal end of an endoscope in which a stapler device 701 and a tissue acquisition tool 754 are being utilized to manipulate and couple tissue 770. Since stapler device 701 is angled relative to the longitudinal axis of the endoscope, the field of view includes a view of the space between the anvil and the body of stapler device 701, facilitating the positioning of tissue 770 between the anvil and body for stapling.

Figure 8:
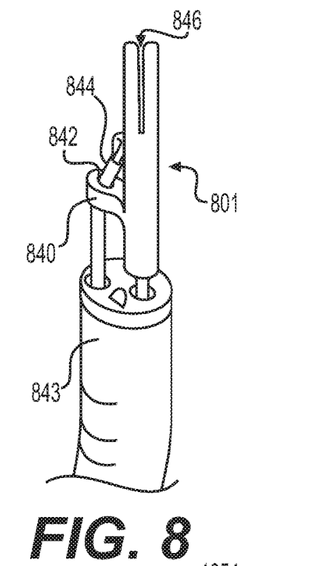
FIG. 8 is a perspective view of an exemplary surgical stapler system, according to aspects of this disclosure.

FIG. 8 shows an example of an alternative embodiment of a stapler device 801 including a guide protrusion 840. Guide protrusion 840 may include a lumen 842 configured to receive a tissue acquisition tool 844. Tissue acquisition tool 844 may be positioned within lumen 842 of guide protrusion 840 prior to inserting endoscope 843 into a patient's body. Tool 844 and stapler device 801 can be backloaded into one or more lumens of endoscope 843. Pre-aligning a tissue acquisition tool 844 within guide protrusion's lumen 842 may facilitate positioning tissue acquisition tool 844 within the space 846 between stapler device's 801 anvil and body (i.e. stapler device's active region), and may guide tissue acquisition tool 844 towards stapler device 801 when translated. Lumen 842 may be curved or otherwise angled towards stapler device 801 to bend tissue acquisition tool 844 towards stapler device 801. For example, the plane of the distal opening of lumen 842 may be angled to face the stapler device's active region. Guide protrusion 840 may extend radially away from a portion of stapler device 801 that is proximal to stapler device's 801 anvil or space 846. Guide protrusion 840 may be fixed to stapler device 801. In some examples, guide protrusion 840 may be rigid or may be semi-rigid. Guide protrusion 840 may include a lumen 842 that includes a central longitudinal axis that is spaced from the longitudinal axis of stapler device 801.

Figure 9:
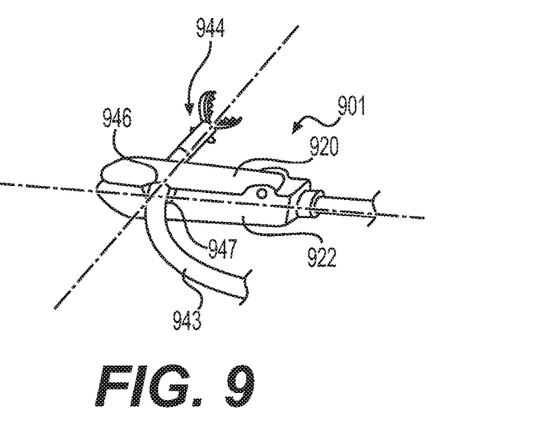
FIG. 9 is a perspective view of an exemplary surgical stapler system, according to aspects of this disclosure.

FIG. 9 shows an exemplary embodiment of a stapler device 901 including anvil 920, body 922, recess 946 in anvil 920, and recess 947 in body 922. Recesses 946, 947 may be positioned on radially inward facing surfaces of anvil 920 and body 922 respectively, opposing each other and may form a lumen between anvil 920 and body 922 when anvil 920 and body 922 are in a closed position that lumen traverses the longitudinal axis of stapler device 901. A tissue acquisition tool 944 may be positioned within lumen recesses 946, 947 when stapler device 901 is in a closed position such that when elongated body 943 of tissue acquisition tool 944 is translated proximally, the distal end of tissue acquisition tool 944 is moved into the space between anvil 920 and body 922. Pre-positioning tissue acquisition tool 944 within the space between anvil 920 and body 922, or within the active portion of stapler device 901, may allow a user to more easily position the distal end of tissue acquisition tool 944 and tissue within the active portion of stapler device 901. Tissue acquisition tool 944 may be preloaded into the lumen formed by recesses 946, 947 prior to insertion into a patient's body.

Figure 10A:
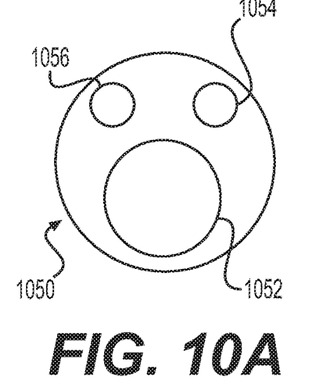
FIG. 10A is a front view of an exemplary endoscope overset, according to aspects of this disclosure.
Figure 10B:
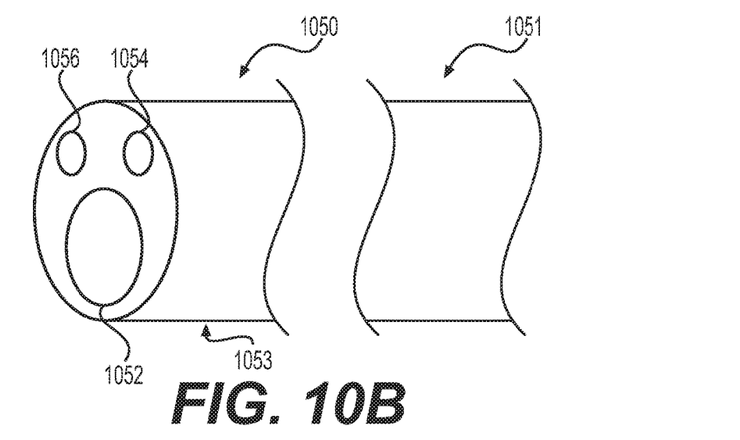
FIG. 10B is a side perspective view of an exemplary endoscope overset, according to aspects of this disclosure.
Figure 11:
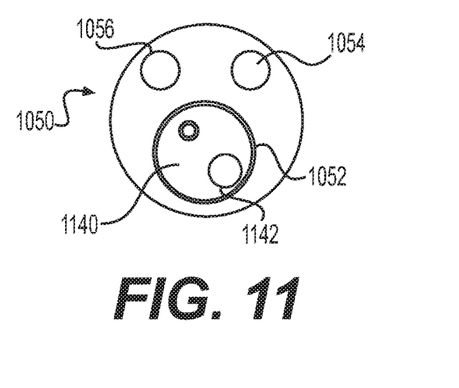
FIG. 11 is a front view of an endoscope system including an endoscope overset, according to aspects of this disclosure.
Figure 12:
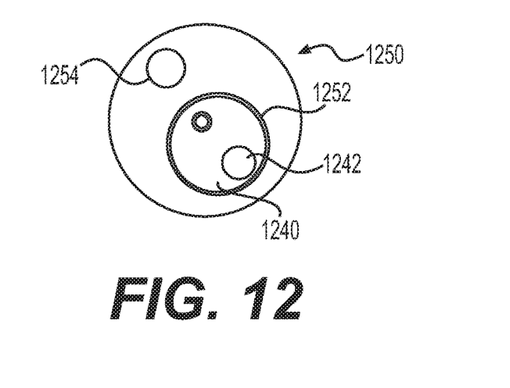
FIG. 12 is a front view of an endoscope system including an endoscope overset, according to aspects of this disclosure.
Figure 13:
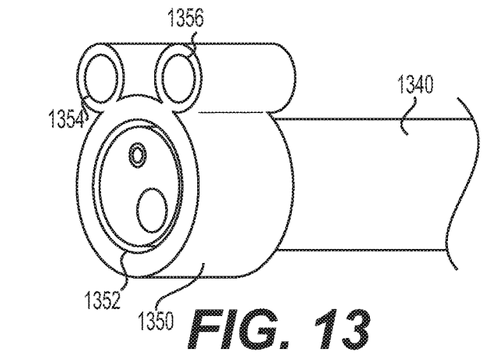
FIG. 13 is a side perspective view of an exemplary endoscope overset, according to aspects of this disclosure.
Figure 14:
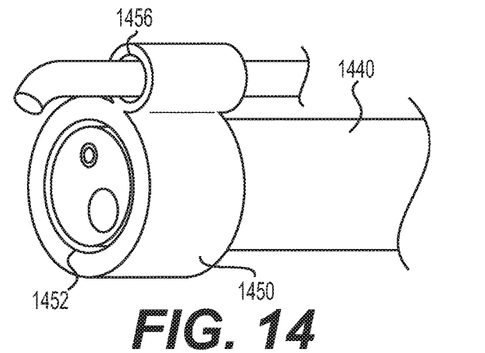
FIG. 14 is another a side perspective view of an exemplary endoscope overset, according to aspects of this disclosure.

FIGS. 10A and 10B show front and side perspective views of an exemplary multi-lumen oversheath 1050 including shaft 1051, distal end portion 1053, lumens 1052, 1054, and 1056. Oversheath 1050 may provide a user with means for utilizing a tissue acquisition tool, a stapling device, and a steerable visualization tool, such as an endoscope that includes a camera. FIG. 11 shows a front view of oversheath 1050 with an endoscope 1140 positioned within lumen 1052. Since endoscope 1140 includes a single working channel 1142, oversheath 1050 provides the user with three total working channels, i.e. lumens 1054, 1056 and working channel 1142. FIG. 12 shows another exemplary embodiment of an oversheath 1250 including two lumens 1252, 1254 with an endoscope 1240 positioned within lumen 1252. Since endoscope 1240 includes a working channel 1242, the oversheath 1250 provides an additional working channel (i.e. lumen 1254) for the user to utilize. Each of oversheath 1050 and 1250 may extend along the entire length of the endoscope 1140, 1240. In other examples, oversheath 1050, 1250 may extend along only a portion of endoscope 1140, 1240. For example, FIGS. 13 and 14 show alternative embodiments of oversheaths 1350, 1450 with lumens 1352, 1354, 1356, 1452, 1456. Oversheaths 1350, 1450 extend along only a portion of the distal end of an endoscope that they are positioned over, such as distal ends of endoscope 1340 or endoscope 1440 shown in FIGS. 13 and 14. Positioning either a stapler device or a tissue acquisition tool within a lumen of an oversheath may move the device or tool farther radially away from the center of the field of view of a camera at the distal end of an endoscope, and may provide a less obstructed view of target tissue the user seeks to position in the active region of the stapler.

Figures 15, 16:
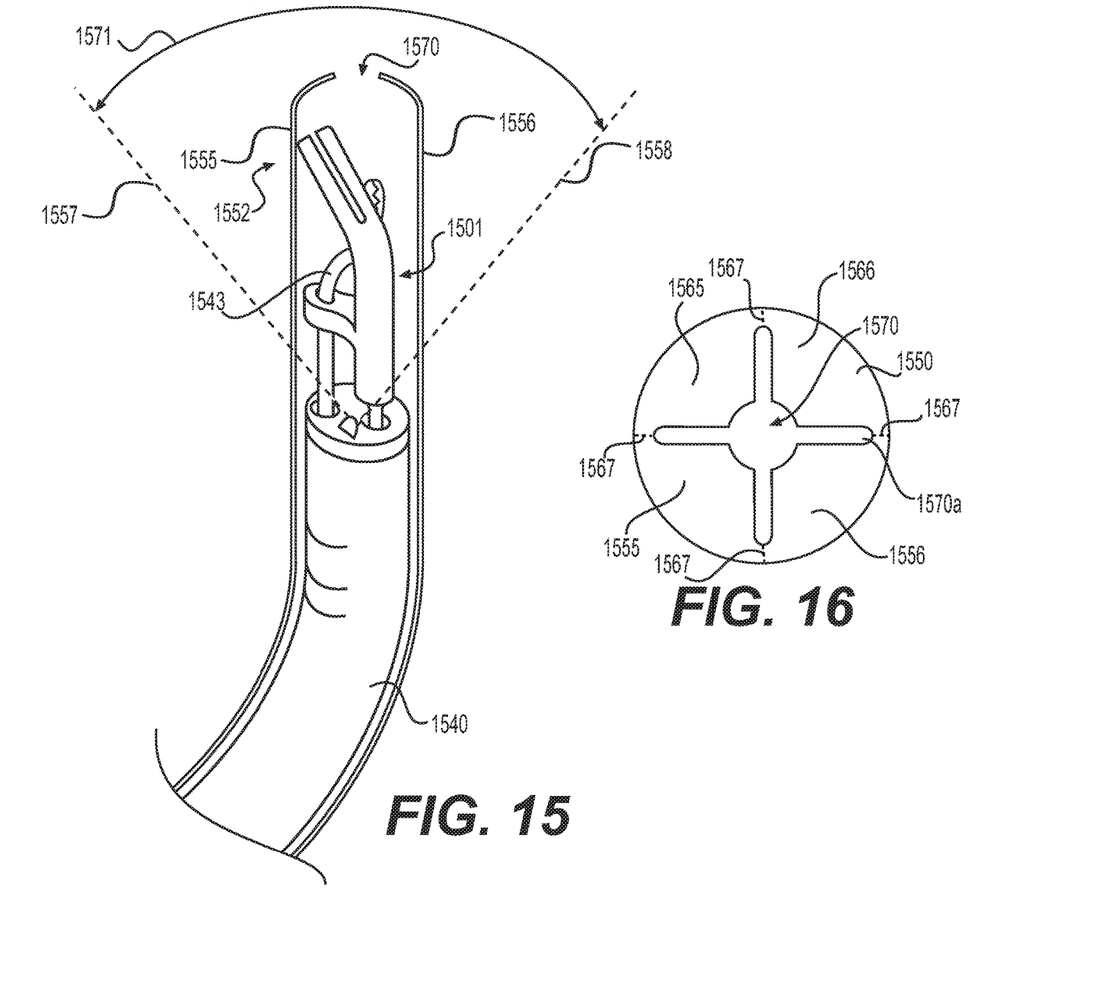
FIG. 15 is a side perspective view of an exemplary endoscope system including an overset shown in cross-section, according to aspects of the present disclosure.
FIG. 16 is a front view of the overset shown in FIG. 15, according to aspects of the present disclosure.

In some examples, an oversheath may be used to protect the patient's tissue from unwanted contact with devices at the distal end of an endoscope while the endoscope travels through the patient's body. FIG. 15 shows an exemplary oversheath 1552 positioned over an endoscope 1540. Extending distally from the distal end of endoscope 1540 are stapler device 1501 and tissue acquisition tool 1543, much like the devices shown in FIG. 8, though any tools may be used with oversheath 1552. Oversheath 1552 is positioned over stapler device 1501 and tissue acquisition tool 1543, and may prevent stapler device 1501 and tissue acquisition tool 1543 from contacting tissue and/or moving radially outward from the longitudinal axis of endoscope 1540, as endoscope 1540 moves through a patient's body. An opening 1570 at the distal end of oversheath 1552 may provide the user with the ability to view in front of the endoscope 1540 while the endoscope 1540 and oversheath 1552 move through a patient's body. Opening 1570 may include one or more proximally extending slots 1570a (4 shown in FIG. 16). Distal portions 1555, 1556 of oversheath 1552 may be movable and flexible to expand and contract opening 1570. An exemplary expanded state of opening 1570 is shown as opening 1571 with dotted lines 1557, 1558 representing distal portions 1555, 1556 after having moved radially outward. Distal portions 1555, 1556 may move radially outwardly to form an expanded state in order to allow a user to access a target area with stapler device 1501 and tissue acquisition tool 1543. To assist radially outward movement of distal portion 1555, 1556, oversheath 1552 may include longitudinal slits 1567 that can be torn. For example, a tearable slit 1567 may extend from each of slots 1570a proximally a distance sufficient to allow separation of portions 1555, 1556 (e.g. to the distal face of endoscope 1540).

In other examples, distal portions 1555, 1556 may be movable to allow the user to pull oversheath 1550 proximally and position stapler device 1501 and tissue acquisition tool 1543 within a target area. As shown in FIG. 16, oversheath 1550 may include four distal portions 1555, 1556, 1565, 1566 that may be moveable. In some examples, each of distal portions 1555, 1556, 1565, 1566 of oversheath 1550 may be configured to move proximally or distally relative to endoscope 1540 to allow a user to uncover or cover stapler device 1501 and tissue acquisition tool 1543. In some examples, distal portions 1555, 1556, 1565, 1566 may move radially outward to expand opening 1570 in order to allow acquisition tool 1543 and stapler device 1501 to pass through opening 1570. For example, distal portions 1555, 1556, 1565, 1566 may move radially outward when contacted by the stapler device 1501 and/or acquisition tool 1543 as the oversheath 1552 is translated proximally. In some examples, oversheath 1550 may be transparent/clear to allow a user to see through oversheath 1550 as endoscope 1540 moves through a patient's body.

Figure 17:
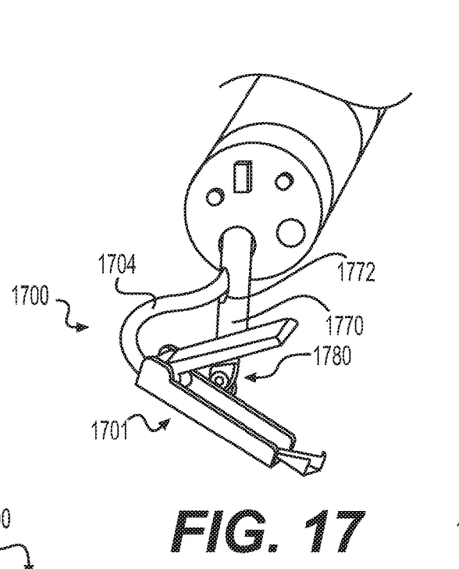
FIG. 17 is a perspective view of a surgical system including an endoscope and an exemplary medical device, according to aspects of the present disclosure.
Figure 18:
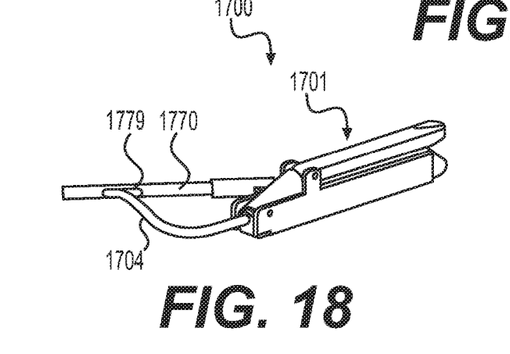
FIG. 18 is a perspective view of the medical device shown in FIG. 17, according to aspects of the present disclosure.
Figure 19:
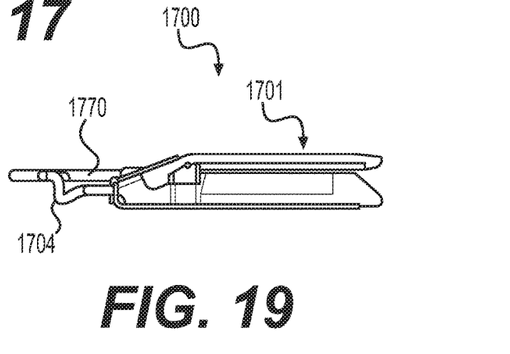
FIG. 19 is a side view of the medical device shown in FIG. 17, according to aspects of the present disclosure.
Figure 20:
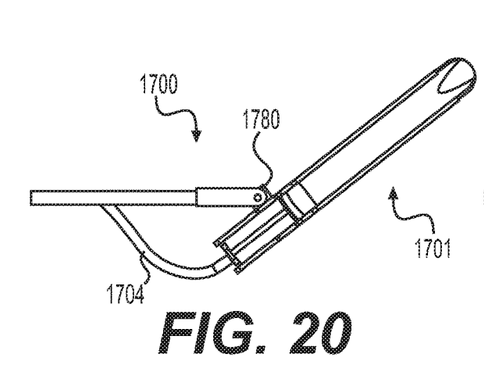
FIGS. 20 and 21 are top views of the medical device shown in FIG. 17, according to aspects of the present disclosure.
Figure 21:
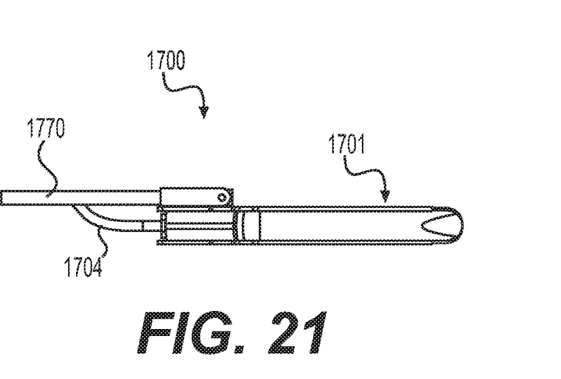

FIG. 17 shows an exemplary medical apparatus 1700 including a stapler device 1701, an elongate body 1704, an elongate rod 1770 including a lumen 1772, and a rotatable connector 1780. The stapler device 1701 and elongate body 1704 may include any of the features and characteristics discussed hereinabove. Rod 1770 may be rigid and may be manufactured from polyether ether ketone (PEEK) or other suitable materials. Elongate body 1704 may be a non-compressible member, such as a Bowden cable, and may include a lumen (not shown) for receiving actuation wires and other components of stapler device 1701. Lumen 1772 of rod 1770 may extend longitudinally from a proximal end to a distal portion of rod 1770. In some examples, lumen 1772 may receive elongate body 1704 and may be configured to allow elongated body to move proximally and distally through lumen 1772. Body 1704 may extend out of lumen 1772 via an opening 1779 in a side wall of rod 1770. Rotatable connector 1780 may couple stapler device 1701 to rod 1770 and may be positioned between the proximal and distal ends of stapler device 1701. In some examples, rotatable connector 1780 permits pivoting of stapler device 1701 relative to rod 1770 such that stapler device 1701 may move between a position where the longitudinal axis of stapler device 1701 is parallel with the longitudinal axis of rod 1770 and a position where the longitudinal axis of stapler device 1701 is transverse to the longitudinal axis of rod 1770. In embodiments, rotatable connector 1780 may permit such pivoting so that the angle between the longitudinal axes is greater than zero degrees and up to as much as 180 degrees, where the longitudinal axis of stapler device 1701 is parallel with the longitudinal axis of rod 1770. FIGS. 18-21 show various views of medical apparatus 1700 with stapler device 1701 rotated various degrees relative to rod 1770. As shown in FIGS. 18 and 19, lumen opening 1779 may be oval shaped and may be elongate in the longitudinal direction of rod 1770 to allow elongate body 1704 to smoothly transition into and out of rod 1770 and to minimize friction between lumen opening 1779 and elongate body 1704 when elongate body 1704 moves through lumen opening 1779. A user may pivot stapler device 1701 by pushing or pulling on elongate body 1704 (to move elongated body 1704 proximally or distally), which then pushes or pulls on stapler device 1701 and causes stapler device 1701 to rotate about rotatable connector 1780. In some embodiments, rotatable connector 1780 may include a pin extending through a device at a distal end of rod 1770 and a flange extending from stapler device 1701. Stapler device 1701 may include a pair of flanges extending from a portion of its body that include apertures for a pin, and rod 1770 may include a device extending from a distal end of rod 1770 including an aperture that is configured to align with the apertures of the pair of flanges, and a pin may be positioned with the apertures of the pair of flanges and the aperture of the device extending from a distal end of rod 1770 to form rotatable connector 1780.

Each of the aforementioned apparatuses and devices may be used to visualize, couple, and/or cut tissue. In some examples, a user may load an elongate body of a stapler device in a working channel of an endoscope by backfeeding the elongate body through a distal end of an endoscope working channel to position a portion of the elongate body within the working channel. Once the elongate body is positioned within a working channel, a handle assembly may be coupled to the proximal end of the elongate body. The user may then introduce the endoscope into the patient's body and move the endoscope towards a target area. The user may locate a target area (such as a tumor or other diseased tissue) present in a body lumen of a subject using the endoscope by directly visualizing the target area using an image sensor. Once the user has positioned the endoscope's distal end proximate to a target area, the user may position a tissue acquisition tool within a working channel of the endoscope, if such a tool is not already present. In some examples, if the user placed an oversheath over the endoscope prior to insertion of the endoscope into the patient's body, the user may move the oversheath proximally to expose the stapler device to the target area and/or tear away portions of the oversheath to expose the stapler device. When the distal end of the endoscope is positioned at the target area, the user may actuate the stapler device to an open position creating a space between the stapler's anvil and body. The user may then introduce the tissue acquisition tool to the target area and position the tissue acquisition tool between or close to the active portion of the stapler device, e.g. the space between the stapler device's anvil and body. The user may then grasp tissue with the tissue acquisition tool and move tissue into the stapler device's active portion. Once tissue is positioned within the stapler device's active portion, the user may move the stapler device's anvil and body to a closed position and clamp down on the grasped tissue with the stapler device. The user may then actuate an actuator in order to pull on an actuation wire, thus moving an actuation sled of the stapler device proximally. By moving the actuation sled proximally via an actuator, the user may deploy fasteners into the clamped tissue and against the stapler device's anvil. In some examples, the user may actuate a knife in the stapler device to cut portions of the target tissue either before or after fastening tissue together via fasteners.

By providing a stapler instrument that includes a flexible body while still able to effectively staple tissue, the user may be able to increase visualization of the target tissue and may prevent unwanted stapling errors, such as stapling within portions of contagious tissue. The increased visualization from a maneuverable, flexible stapler also may aid in ensuring that as much of or all of a target lesion is removed.

It will be apparent to those skilled in the art that various modifications and variations may be made in the disclosed devices and methods without departing from the scope of the disclosure. Other aspects of the disclosure will be apparent to those skilled in the art from consideration of the specification and practice of the features disclosed herein. It is intended that the specification and examples be considered as exemplary only.

We claim:

1. A tissue fastening device comprising:
   a handle assembly including at least two actuators;
   a first body extending distally from the handle assembly;
   a fastening device coupled to a distal end of the first body, wherein the fastening device comprises:
      a longitudinal body including a channel;
      a cartridge that includes a plurality of fasteners, wherein the channel receives the cartridge; and
      an anvil mounted adjacent the cartridge;
   a second body including a lumen, wherein the first body is positioned in, movable within, and extends from the lumen; and
   a coupler coupling a distal end of the second body to the fastening device, wherein the fastening device is pivotable about the coupler as a proximal portion of the first body is moved proximally and/or distally;
   wherein, in a first configuration, a distal portion of the first body has a first angle relative to a longitudinal axis of the second body and wherein, in a second configuration, a distal portion of the first body has a second angle relative to the longitudinal axis of the second body.

2. The device of claim 1, wherein the second body defines an opening in a side wall of the second body and through which the first body extends.

3. The device of claim 2, wherein the opening is oval-shaped.

4. The device of claim 1, wherein the handle assembly includes a first actuator configured to move longitudinally in proximal and distal directions and a second actuator configured to pivot relative to a body of the handle assembly.

5. The device of claim 1, wherein the first body includes a lumen.

6. The device of claim 1, wherein the coupler couples the distal end of the second body to a side of either the longitudinal body or the anvil, between a proximal end of (a) the longitudinal body or (b) the anvil and a distal end of the (a) longitudinal body or (b) the anvil.

7. The device of claim 6, wherein the second body is rigid.

8. The device of claim 1, wherein the coupler includes (a) a flange extending from the longitudinal body or the anvil and (b) a pin extending through the flange.

9. The device of claim 8, wherein the distal end of the second body includes an opening through which the pin passes.

10. The device of claim 1, wherein a distal end of the second body is distal to a distal end of the first body in at least one of the first configuration or the second configuration.

11. The device of claim 1, wherein a longitudinal axis of the fastening device is parallel to a longitudinal axis of the second body in the at least one of the first configuration or the second configuration.

12. A tissue fastening device comprising:
   a handle assembly including at least two actuators;
   a first body extending distally from the handle assembly;
   a fastening device coupled to a distal end of the first body, wherein the fastening device comprises:
      a longitudinal body including a channel;
      a cartridge that includes a plurality of fasteners, wherein the channel receives the cartridge; and
      an anvil mounted adjacent the cartridge;
   a second body including a lumen, wherein the first body is positioned in, movable within, and extends from the lumen; and
   a coupler coupling a distal end of the second body to a side of either the longitudinal body or the anvil, between a proximal end of (a) the longitudinal body or (b) the anvil and a distal end of (a) the longitudinal body or (b) the anvil, wherein the fastening device is pivotable about the coupler as a proximal portion of the first body is moved proximally and/or distally.

13. The device of claim 12, wherein the second body defines an oval-shaped opening in a side wall of the second body, through which the first body extends.

14. The device of claim 12, wherein the coupler includes (a) a flange extending from the longitudinal body or the anvil and (b) a pin extending through the flange.

15. The device of claim 14, wherein the distal end of the second body includes an opening through which the pin passes.

16. The device of claim 12, wherein a distal end of the second body is distal to a distal end of the first body in a configuration in which a longitudinal axis of the fastening device is parallel to a longitudinal axis of the second body.

17. The device of claim 12, wherein the second body is rigid.

18. A tissue fastening device comprising:
 a handle assembly including at least two actuators;
 a first body extending distally from the handle assembly;
 a fastening device coupled to a distal end of the first body, wherein the fastening device comprises:
  a longitudinal body including a channel;
  a cartridge that includes a plurality of fasteners, wherein the channel receives the cartridge; and
  an anvil mounted adjacent the cartridge;
 a second body including a lumen, wherein the first body is positioned in, movable within, and extends from the lumen; and
 a coupler coupling a distal end of the second body to the fastening device, wherein the fastening device is pivotable about the coupler as a proximal portion of the first body is moved proximally and/or distally;
 wherein a distal end of the second body is distal to a distal end of the first body in at least one configuration of the first body.

19. The device of claim 18, wherein the at least one configuration includes a longitudinal axis of the fastening device parallel to a longitudinal axis of the second body.

20. The device of claim 18, wherein the second body is rigid.

* * * * *